United States Patent
Alqahtani et al.

(10) Patent No.: US 10,407,359 B2
(45) Date of Patent: Sep. 10, 2019

(54) PROCESS FOR DEACTIVATION OF AN OLEFIN OLIGOMERIZATION CATALYST

(71) Applicant: SABIC Global Technologies B.V., Bergen op Zoom (NL)

(72) Inventors: Abdullah Alqahtani, Riyadh (SA); Anina Wöhl, München (DE); Wolfgang Müller, München (DE); Marco Harff, München (DE); Heinz Bölt, Wolfratshausen (DE); Andreas Metzner, Dresden (DE); Ralf Noack, Dresden (DE); Lars-Erik Gärtner, Dresden (DE); Andreas Meiswinkel, Prien (DE)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/760,383

(22) PCT Filed: Sep. 13, 2016

(86) PCT No.: PCT/IB2016/055449
§ 371 (c)(1),
(2) Date: Mar. 15, 2018

(87) PCT Pub. No.: WO2017/046701
PCT Pub. Date: Mar. 23, 2017

(65) Prior Publication Data
US 2018/0258009 A1    Sep. 13, 2018

Related U.S. Application Data

(60) Provisional application No. 62/219,424, filed on Sep. 16, 2015.

(51) Int. Cl.
*C07C 2/22*    (2006.01)
*C07C 2/26*    (2006.01)
(Continued)

(52) U.S. Cl.
CPC ............... *C07C 2/32* (2013.01); *B01J 31/143* (2013.01); *B01J 31/189* (2013.01); *B01J 31/34* (2013.01);
(Continued)

(58) Field of Classification Search
None
See application file for complete search history.

(56) References Cited

U.S. PATENT DOCUMENTS

| 5,689,028 A | 11/1997 | Lashier et al. |
| 8,344,198 B2 | 1/2013 | Ewert et al. |

(Continued)

FOREIGN PATENT DOCUMENTS

| DE | 4338414 C1 | 3/1995 |
| DE | 19807226 A1 | 10/1998 |

(Continued)

OTHER PUBLICATIONS

A. Meiswinkel, A. Wohl, W. Muller, H.V. Bolt, F.M. Mosa and M. H. Al-Hazmi, "Developing Linear-alpha-Olefins Technology—From Laboratory to a Commercial Plant", Oil Gas European MAgazine, Feb. 2012.

(Continued)

*Primary Examiner* — In Suk C Bullock
*Assistant Examiner* — Ali Z Fadhel
(74) *Attorney, Agent, or Firm* — Cantor Colburn LLP

(57) ABSTRACT

A process for deactivation of an olefin oligomerization catalyst is described, including contacting a catalyst composition with a catalyst quenching medium to form a deactivated catalyst composition, and recovering excess catalyst quenching medium. The catalyst quenching medium includes an alcohol having at least 6 carbon atoms, an organic amine, an amino alcohol, or a combination comprising at least one of the foregoing. The catalyst quenching (Continued)

medium is present in a molar ratio of catalyst quenching medium to catalyst of at least 3:1. A process for the oligomerization of an olefin is also described, including feeding the olefin, a solvent, and a catalyst composition into a reactor, oligomerizing the olefin in the reactor to form a reaction product stream including linear alpha olefins, solvent, and the catalyst composition, and contacting the reaction product stream with a catalyst quenching medium.

20 Claims, 1 Drawing Sheet

(51) Int. Cl.
*C07C 2/32* (2006.01)
*B01J 31/14* (2006.01)
*B01J 31/18* (2006.01)
*B01J 31/34* (2006.01)
*C07C 11/02* (2006.01)
*C07C 11/08* (2006.01)
*C07C 11/107* (2006.01)

(52) U.S. Cl.
CPC .................. *C07C 2/22* (2013.01); *C07C 2/26* (2013.01); *B01J 2231/20* (2013.01); *B01J 2531/62* (2013.01); *C07C 2527/132* (2013.01); *C07C 2531/14* (2013.01); *C07C 2531/22* (2013.01)

(56) References Cited

U.S. PATENT DOCUMENTS

| 2010/0190939 A1* | 7/2010 | Fritz | B01J 31/143 |
| | | | 526/126 |
| 2011/0046429 A1 | 2/2011 | Vugar et al. | |
| 2015/0291486 A1* | 10/2015 | Weber | C07C 2/30 |
| | | | 585/512 |

FOREIGN PATENT DOCUMENTS

| EP | 2234945 B1 | 7/2009 |
| EP | 2287142 A1 | 7/2009 |
| EP | 2106854 A1 | 10/2009 |
| EP | 2489431 A1 | 2/2011 |
| EP | 2239056 B1 | 7/2011 |
| WO | 2004056479 A1 | 7/2004 |
| WO | 2009006979 A2 | 1/2009 |
| WO | 2009095147 A1 | 8/2009 |
| WO | 2011156892 A2 | 12/2011 |
| WO | 2017011127 A1 | 1/2017 |

OTHER PUBLICATIONS

International Search Report for International Application No. PCT/IB2016/055449; International filing date: Sep. 13, 2016; dated Dec. 21, 2016; 5 pages.
Written Opinion of the International Searching Authority for International Application No. PCT/IB2016/055449; International filing date: Sep. 13, 2016; dated Dec. 21, 2016; 6 pages.

* cited by examiner

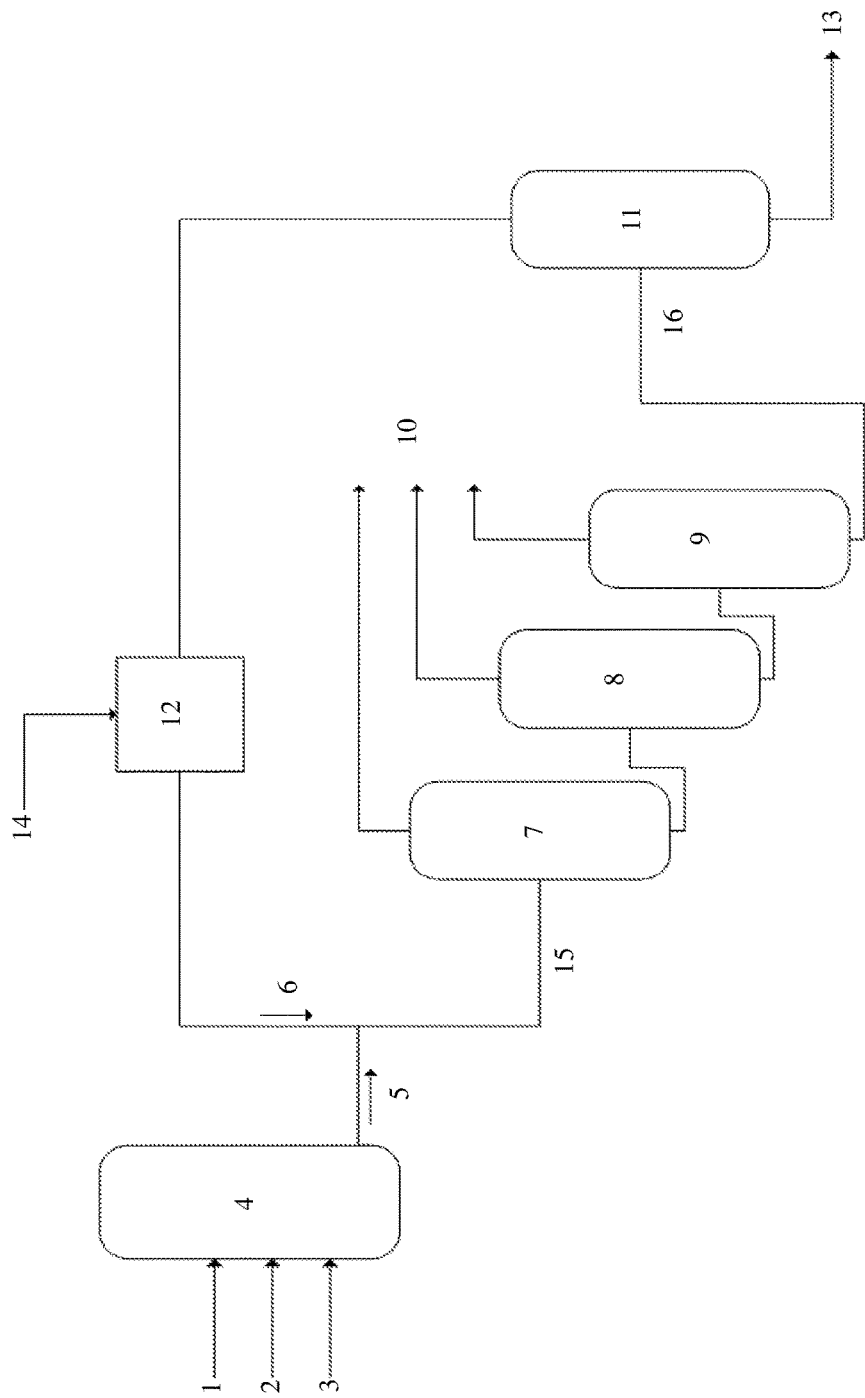

PROCESS FOR DEACTIVATION OF AN OLEFIN OLIGOMERIZATION CATALYST

CROSS-REFERENCE TO RELATED APPLICATIONS

This application is a National Stage application of PCT/IB2016/055449, filed Sep. 13, 2016, which claims the benefit of U.S. Provisional Application No. 62/219,424, filed Sep. 16, 2015, both of which are incorporated by reference herein in their entirety.

BACKGROUND

Linear alpha olefins (LAOs) are olefins with a chemical formula $C_xH_{2x}$, distinguished from other mono-olefins with a similar molecular formula by linearity of the hydrocarbon chain and the position of the double bond at the primary or alpha position. Linear alpha olefins comprise a class of industrially important alpha-olefins, including 1-butene, 1-hexene, 1-octene, 1-decene, 1-dodecene, 1-tetradecene, 1-hexadecene, 1-octadecene and higher blends of $C_{20}$-$C_{24}$, $C_{24}$-$C_{30}$, and $C_{20}$-$C_{30}$ olefins. Linear alpha olefins are very useful intermediates for the manufacture of detergents, synthetic lubricants, copolymers, plasticizers, and many other important products. Existing processes for the production of linear alpha olefins typically rely on the oligomerization of ethylene.

Processes for the oligomerization of ethylene utilizing a homogenous catalyst are widely known. For example, DE 43 38 414 C1 discloses a process for the oligomerization of ethylene to obtain linear alpha-olefins, where ethylene is catalytically converted in an empty tubular reactor utilizing a catalyst comprising a zirconium component and an aluminum component. The process is advantageously carried out in a continuous mode wherein gaseous and liquid outlet streams are obtained. The liquid outlet stream usually contains solvent, catalyst, dissolved ethylene and linear alpha-olefins. The catalyst can be preferably deactivated by caustic. Preferably, the deactivated catalyst is also extracted from the phase containing solvent, ethylene and alpha-olefins. DE 198 07 226 A1 discloses the deactivation of the oligomerization catalyst with an aqueous solution of sodium hydroxide (caustic), wherein the deactivated catalyst is transferred from the organic phase into the aqueous phase.

It is generally preferred to carry out the catalyst deactivation in a fast and effective manner to reduce or eliminate product degradation through various side reactions, ultimately affecting product purity. A disadvantage of known techniques is that during the catalyst deactivation and removal, hydrochloric acid (HCl) is formed, which can catalyze isomerization of linear alpha olefins. A further disadvantage of known catalyst deactivation processes includes the formation of organic chlorides and alkylated toluene byproducts.

Therefore, there remains a need for an improved method of catalyst deactivation for an olefin oligomerization catalyst that can overcome the above-described limitations of presently known methods.

BRIEF DESCRIPTION

Disclosed in various embodiments are processes for deactivation of an olefin oligomerization catalyst and a process for the oligomerization of an olefin.

A process for deactivation of an olefin oligomerization catalyst comprises: contacting a catalyst composition with a catalyst quenching medium comprising an alcohol having at least 6 carbon atoms, an organic amine, an amino alcohol, or a combination comprising at least one of the foregoing, to form a deactivated catalyst composition, wherein the catalyst quenching medium is present in a molar ratio of catalyst quenching medium to catalyst of at least 3:1, preferably at least 5:1, more preferably at least 100:1; and recovering excess catalyst quenching medium.

A process for the oligomerization of an olefin comprises feeding the olefin, a solvent, and a catalyst composition comprising a chromium source, a heteroatomic multidentate ligand, and an activator into a reactor; oligomerizing the olefin in the reactor to form a reaction product stream comprising linear alpha olefins, the solvent, and the catalyst composition; contacting the reaction product stream with a catalyst quenching medium comprising an alcohol having at least 6 carbon atoms, an organic amine, an amino alcohol, or a combination comprising at least one of the foregoing, to form a first intermediate stream comprising a deactivated catalyst composition, linear alpha olefins, the solvent, and excess catalyst quenching medium; separating the linear alpha olefins from the first intermediate stream to provide a second intermediate stream comprising the deactivated catalyst composition and excess catalyst quenching medium; and recovering the catalyst quenching medium from the second intermediate stream; wherein the catalyst quenching medium is contacted with the reaction product stream in a moles of catalyst quenching medium to moles of chromium source and activator ratio of at least 3:1, preferably at least 5:1, more preferably at least 100:1.

The above described and other features are exemplified by the following FIGURE and detailed description.

BRIEF DESCRIPTION OF THE DRAWING

The following is a brief description of the drawing wherein like elements are numbered alike and which is presented for the purposes of illustrating the exemplary embodiments disclosed herein and not for the purposes of limiting the same.

FIG. 1 shows a schematic representation of a process for oligomerization of an olefin including olefin oligomerization catalyst deactivation.

DETAILED DESCRIPTION

Described herein is a process for deactivation of an olefin oligomerization catalyst. It was unexpectedly discovered that employing a carefully selected catalyst quenching medium in stoichiometric excess relative to the active catalyst components can effectively deactivate the olefin oligomerization catalyst. In a particularly advantageous feature, the large excess of catalyst quenching medium can also reduce or eliminate the deposition of heavy fractions (e.g., greater than $C_{12}$ olefins), waxes, and polymer byproducts of an oligomerization process in downstream equipment. Furthermore, the catalyst quenching medium can be separated from the linear alpha olefin products, solvents, and other reaction components by known distillation techniques. Recovered catalyst quenching medium can be recycled, leading to significantly reduced costs associated with catalyst deactivation for an olefin oligomerization process.

Accordingly, one aspect of the present disclosure is a process for deactivation of an olefin oligomerization catalyst. The process comprises contacting a catalyst composition with a catalyst quenching medium to form a deactivated catalyst composition, and recovering excess catalyst quenching medium. In some embodiments, the process can further include recycling the recovered catalyst quenching medium, for example the recovered catalyst quenching medium can be used to form a deactivated catalyst composition in a subsequent process.

The catalyst composition can be any catalyst system known for the oligomerization of ethylene as described in further detail below, and which includes a chromium source, a heteroatomic multidentate ligand, and an activator, also known as a co-catalyst. A catalyst modifier is not required, but is also preferably present.

The chromium compound can be an organic or inorganic salts, coordination complex, or organometallic complex of Cr(II) or Cr(III). In some embodiments the chromium compound is $CrCl_3(tetrahydrofuran)_3$, Cr(III)acetylacetonate, Cr(III)octanoate, chromium hexacarbonyl, Cr(III)-2-ethylhexanoate, benzene(tricarbonyl)-chromium, or Cr(III)chloride. A combination of different chromium compounds can be used.

The heteroatomic multidentate ligand includes two or more heteroatoms (P, N, O, S, As, Sb, Bi, O, S, or Se) that can be the same or different, wherein the two or more heteroatoms are linked via a linking group. The linking group is a $C_{1-6}$ hydrocarbylene group or one of the foregoing heteroatoms. Any of the heteroatoms in the ligand can be substituted to satisfy the valence thereof, with a hydrogen, halogen, $C_{1-18}$ hydrocarbyl group, $C_{1-10}$ hydrocarbylene group linked to the same or different heteroatoms to form a heterocyclic structure, amino group of the formula $NR^aR^b$ wherein each of $R^a$ and $R^b$ is independently hydrogen or a $C_{1-18}$ hydrocarbyl group, a silyl group of the formula $SiR^aR^bR^c$ wherein each of $R^a$, $R^b$, and $R^c$ is independently hydrogen or a $C_{1-18}$ hydrocarbyl group, or a combination comprising at least one of the foregoing substituents. The heteroatoms of the multidentate ligand are preferably a combination comprising phosphorus with nitrogen and sulfur or a combination comprising phosphorous and nitrogen, linked by at least one additional phosphorus or nitrogen heteroatom. In certain embodiments, the ligand can have the backbone PNP, PNPN, NPN, NPNP, NPNPN, PNNP, or cyclic derivatives containing these backbones wherein one or more of the heteroatoms is linked by a $C_{1-10}$ hydrocarbylene to provide a heterocyclic group. A combination of different ligands can be used.

In some embodiments, the ligand has the backbone PNPNH, which as used herein has the general structure $R^1R^2P—N(R^3)—P(R^4)—N(R^5)—H$ wherein each of $R^1$, $R^2$, $R^3$, $R^4$, and $R^5$ is independently a hydrogen, halogen, $C_{1-18}$ hydrocarbyl group, amino group of the formula $NR^aR^b$ wherein each of $R^a$ and $R^b$ is independently hydrogen or a $C_{1-18}$ hydrocarbyl group, a silyl group of the formula $SiR^aR^bR^c$ wherein each of $R^a$, $R^b$, and $R^c$ is independently hydrogen or a $C_{1-18}$ hydrocarbyl group, or two of $R^1$, $R^2$, $R^3$, $R^4$, $R^5$, $R^a$, or $R^b$ taken together are a substituted or unsubstituted $C_{1-10}$ hydrocarbylene group linked to the same or different heteroatoms to form a heterocyclic structure. Exemplary ligands having a heterocyclic structure include the following

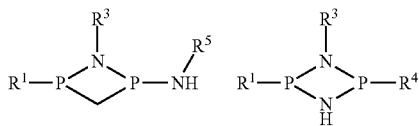

-continued

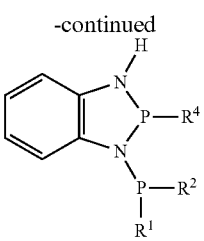

wherein $R^1$, $R^2$, $R^3$, $R^4$, $R^5$ are as described above. In a specific embodiment, each $R^1$, $R^2$, $R^3$, $R^4$, $R^5$ are independently hydrogen, substituted or unsubstituted $C_1$-$C_8$ alkyl, substituted or unsubstituted $C_6$-$C_{20}$ aryl, more preferably unsubstituted $C_1$-$C_6$ alkyl or unsubstituted $C_6$-$C_{10}$ aryl. A specific example of the ligand is $(phenyl)_2PN(iso-propyl)P(phenyl)N(iso-propyl)H$, commonly abbreviated $Ph_2PN(i-Pr)P(Ph)NH(i-Pr)$.

Activators are known in the art, and are commonly aluminum compounds, for example a tri($C_1$-$C_6$alkyl) aluminum such as triethyl aluminum, ($C_1$-$C_6$ alkyl) aluminum sesquichloride, di($C_1$-$C_6$alkyl) aluminum chloride, or ($C_1$-$C_6$-alkyl) aluminum dichloride, or an aluminoxane such as methylaluminoxane (MAO). Each alkyl group can be the same or different, and in some embodiments is methyl, ethyl, isopropyl, or isobutyl. A combination of different activators can be used.

As is known in the art, the modifier can modify the activator, and serve as a chlorine source. Modifiers can include an ammonium or phosphonium salt of the type $(H_4E)X$, $(H_3ER)X$, $(H_2ER_2)X$, $(HER_3)X$, or $(ER_4)X$ wherein E is N or P, X is Cl, Br, or I, and each R is independently a $C_1$-$C_{22}$ hydrocarbyl, preferably a substituted or unsubstituted $C_1$-$C_{16}$-alkyl, $C_2$-$C_{16}$-acyl, or substituted or unsubstituted $C_6$-$C_{20}$-aryl. In some embodiments the modifier is dodecyltrimethylammonium chloride or tetraphenylphosphonium chloride.

In some embodiments, the catalyst composition can be halogen-free. For example, the catalyst composition can be devoid of a halogenated compound, or no halogenated compound is intentionally added to the catalyst composition.

The catalyst composition is often pre-formed, for example by combining the components in a solvent before contacting with ethylene in an oligomerization process. Examples of solvents that can be used include toluene, benzene, ethylbenzene, cumenene, xylenes, mesitylene, $C_4$-$C_{15}$ paraffins, cyclohexane, $C_4$-$C_{12}$ olefins such as butene, hexene, heptene, octene, or ethers or multiethers such as diethylether, tetrahydrofuran, dioxane, di($C_1$-$C_8$ alkyl)ethers. In some embodiments the solvent is an aromatic solvent such as toluene.

The type of each component selected for use in the catalyst composition and relative amount of each component depend on the desired product and desired selectivity. In some embodiments, the concentration of the chromium compound is 0.01 to 100 millimole per liter (mmol/l), or 0.01 to 10 mmol/l, or 0.01 to 1 mmol/l, or 0.1 to 1.0 mmol/l; and the mole ratio of multidentate ligand:Cr compound:activator is 0.1:1:1 to 10:1:1,000, or 0.5:1:50 to 2:1:500, or 1:1:100 to 5:1:300. Suitable catalyst systems are described, for example, in EP2489431 B1; EP2106854 B1; and WO2004/056479.

The above-described catalyst composition can be contacted with a catalyst quenching medium to form a deactivated catalyst composition. The catalyst quenching medium comprises an alcohol having at least 6 carbon atoms, an organic amine, an amino alcohol, or a combination comprising at least one of the foregoing. In some embodiments, the catalyst quenching medium can be an organic amine, preferably a primary or secondary organic amine. For example, the organic amine can have the formula $R^6R^7NH$, wherein $R^6$ and $R^7$ are each independently hydrogen, a $C_{1-12}$ alkyl group, or a substituted or unsubstituted $C_{6-20}$ aryl group. In an embodiment, at least one of $R^6$ or $R^7$ is not a hydrogen. Examples of suitable organic amines can include tert-butyl amine, cyclopentylamine, tert-octylamine, n-heptylamine, 2-heptylamine, hexylamine, 2-ethylhexylamine, dihexylamine, 1,6-diaminohexane, tributylamine, 1,8-diaminooctane, n-dodecylamine, 3-ethylheptylamine, and the like, or a combination comprising at least one of the foregoing. In some embodiments, the catalyst quenching medium is preferably an alcohol having at least 6 carbon atoms, for example a $C_{6-20}$ alkyl alcohol. As used herein, the term "alcohol" includes monoalcohols, diols, and polyols. In some embodiments, the alcohol has a boiling point, or molecular weight, such that the alcohol will not form an azeotrope with the linear alpha olefin product. In some embodiments, the alcohol has a boiling point different from the olefin product in the reactor effluent stream. In some embodiments, the alcohol is a $C_{6-12}$ alkyl alcohol, for example 1-hexanol, 2-hexanol, 3-hexanol, 2-ethyl-1-hexanol, 1-heptanol, 2-heptanol, 3-heptanol, 4-heptanol, 2-methyl-3-heptanol, 1-octanol, 2-octanol, 3-octanol, 4-octanol, 7-methyl-2-decanol, 1-decanol, 2-decanol, 3-decanol, 4-decanol, 5-decanol, 2-ethyl-1-decanol, and combinations comprising at least one of the foregoing. In some embodiments, the catalyst quenching medium comprises 1-decanol.

The process for deactivation of an olefin oligomerization catalyst can advantageously be used in conjunction with any known olefin oligomerization process. Accordingly, another embodiment is a process for the oligomerization of an olefin. The process comprises feeding an olefin, a solvent, and a catalyst composition into a reactor.

The olefin can include any compound having 2 to 30 carbon atoms and at least one olefinic double bond. For example, the olefin can be ethylene, propylene, 1-butene, 2-butene, isobutylene, 1-pentene, 2-pentene, 1-hexene, 2-hexene, 3-hexene, 1-heptene, 2-heptene, 3-heptene, and the like, or a combination comprising at least one of the foregoing. In some embodiments, the olefin is ethylene.

The solvent can be any organic solvent capable of dissolving the reaction components. The solvent is further preferably non-reactive with the catalyst composition. Examples of desirable organic solvents can include, but are not limited to, aromatic hydrocarbon solvents which can be unsubstituted or substituted, for example, toluene, benzene, ethyl benzene, xylene, mesitylene, monochlorobenzene, dichlorobenzene, chlorotoluene, aliphatic paraffin hydrocarbons, for example, pentane, hexane, heptane, octane, nonane, decane, alicyclic hydrocarbon compounds, for example, cyclohexane, decahydronaphthalene, and halogenated alkanes, for example, dichloroethane and dichlorobutane, or a combination comprising at least one of the foregoing. In some embodiments, the solvent can be toluene, xylene, mesitylene, ethyl benzene, n-pentane, n-hexane, cyclohexane, or a combination comprising at least one of the foregoing.

The catalyst composition can include a chromium source, a heteroatomic multidentate ligand, and an activator, wherein each component can be as described above. In some embodiments, the chromium source is $CrCl_3$(tetrahydrofuran)$_3$, Cr(III)acetylacetonate, Cr(III)octanoate, chromium hexacarbonyl, Cr(III)-2-ethylhexanoate, benzene(tricarbonyl)-chromium, Cr(III)chloride, or a combination comprising at least one of the foregoing. In some embodiments, the heteroatomic multidentate ligand is (phenyl)$_2$PN(iso-propyl)P(phenyl)N(iso-propyl)H. In some embodiments, the activator is a tri($C_{1-6}$ alkyl) aluminum, for example triethyl aluminum.

The above described components can be fed into a reactor. The reactor can be any suitable oligomerization reactor generally known in the art. For example, the reactor can be a loop reactor, a plug-flow reactor, a bubble column reactor, or a tubular reactor.

The method further comprises oligomerizing the olefin in the reactor to form a reaction product stream. The reaction product stream comprises linear alpha olefins, the solvent, and the catalyst composition. The linear alpha olefins made by the process disclosed herein can generally be addition products containing greater than or equal to two ethylene units, but not as many ethylene units as in the relatively high molecular weight addition product referred to as polyethylene. In some embodiments, the process can be adapted to be a selective oligomerization process, for example a selective ethylene trimerization or tetramerization process. In some embodiments, the linear alpha olefins comprise $C_{4-12}$ linear alpha olefins. In some embodiments, the linear alpha olefins comprise $C_{4-8}$ linear alpha olefins. For example, the linear alpha olefins can include at least one of 1-butene, 1-hexene, or 1-octene.

Oligomerization can occur at temperatures of 10 to 200° C., for example, 20 to 100° C., for example, 50 to 90° C., for example, 55 to 80° C., for example, 60 to 70° C. Operating pressures can be 1 to 5 MegaPascals (MPa), for example, 2 to 4 MPa. The process can be continuous and mean residence times can be 10 minutes to 20 hours, for example 30 minutes to 4 hours, for example, 1 to 2 hours. Residence times can be chosen so as to achieve the desired conversion at high selectivity.

The reaction product stream can subsequently be contacted with the catalyst quenching medium. The catalyst quenching medium can be an alcohol having at least 6 carbon atoms, an organic amine, an amino alcohol, or a combination comprising at least one of the foregoing, as described above. In some embodiments, the catalyst quenching medium comprises 1-hexanol, 3-hexanol, 2-ethyl-1-hexanol, 3-octanol, 1-heptanol, 2-heptanol, 3-heptanol, 4-heptanol, 2-methyl-3-heptanol, 1-octanol, 2-octanol, 4-octanol, 7-methyl-2-decanol, 1-decanol, 2-decanol, 3-decanol, 4-decanol, 5-decanol, or 2-ethyl-1-decanol, or a combination comprising at least one of the foregoing, preferably 1-decanol. The catalyst quenching medium can be miscible with the reaction product stream.

Contacting the reaction product stream with the catalyst quenching medium can provide a first intermediate stream comprising a deactivated catalyst composition, the linear alpha olefins, the solvent and excess catalyst quenching medium. The catalyst quenching medium is present in a ratio of moles of catalyst quenching medium to total moles of the chromium source and the activator of the catalyst composition of at least 3:1, preferably at least 5:1, more preferably at least 100:1. In some embodiments, the molar ratio of catalyst quenching medium to chromium source and activator can be 3:1 to 200:1, preferably 5:1 to 100:1, more preferably 100:1 to 200:1.

The linear alpha olefins can be separated from the first intermediate stream to provide a second intermediate stream comprising the deactivated catalyst composition and excess catalyst quenching medium. The separating can be by any removal process that is generally known, including, for example, distillation. The presence of the large excess of the catalyst quenching medium during separation of the main product fraction comprising the linear alpha olefins can be particularly useful in preventing undesirable deposition of heavy fractions (e.g., greater than $C_{12}$ olefins), waxes, and polymer byproducts (e.g., polyethylene) in the separation equipment, for example in the bottoms or reboilers of a rectification column used for distillation. Since the catalyst quenching medium preferably has a significantly higher boiling point than the linear alpha olefin products, excess catalyst quenching medium will remain in liquid form, serving as a solvent for the heavy fractions, waxes, and polymer byproducts. This can be particularly advantageous in selective oligomerization processes including selective ethylene tri- and tetramerization processes, where the amount of long chain olefins that can act as solvents for the waxes and polymers is significantly reduced.

The method further comprises recovering catalyst quenching medium from the second intermediate stream. Recovering the catalyst quenching medium can be by, for example distillation. In some embodiments, at least 60%, for example, at least 75%, for example, at least 90% of the catalyst quenching medium is recovered. Separating the linear alpha olefins and recovering the catalyst quenching medium can occur in the same or different rectification columns. In some embodiments, separating the linear alpha olefins and recovering the catalyst quenching medium occur in different rectification columns. In an advantageous aspect of the present disclosure, the recovered catalyst quenching medium can be recycled, for example recycled to the reactor outlet for use as a catalyst quenching medium in subsequent catalyst deactivation processes.

In an embodiment, the oligomerization process can be carried out according to the process depicted in FIG. 1. An olefin 1, a catalyst composition 2, and solvent 3 can be introduced into a reactor 4, where the olefin can be oligomerized. A reaction product stream 5 comprising linear alpha olefin products, the solvent, and the catalyst composition from reactor 4 can be withdrawn from the reactor 4, and contacted with a catalyst quenching medium 6. The resulting stream 15 (referred to as the first intermediate stream) can be introduced into one or more rectification columns 7, 8, 9, to separate main product fractions and solvent, both of which are indicated by reference numeral 10. After product and solvent removal, the resulting second intermediate stream 16 can be introduced to a final rectification column 11 where excess catalyst quenching medium can be recovered and sent to a catalyst quenching medium storage vessel 12, and deactivated catalyst composition, and optionally heavy fractions (e.g., having greater than $C_{12}$ olefins), waxes, and polymer byproducts (e.g., polyethylene) can be withdrawn 13 from a bottom of the rectification column 11. The catalyst quenching medium storage vessel 12 containing recycled catalyst quenching medium can be supplemented with fresh catalyst quenching medium 14 as necessary, and the recycled catalyst quenching medium can advantageously be reused for deactivating an oligomerization catalyst in a reaction product stream 5.

The present disclosure provides an improved process for the deactivation of an olefin oligomerization catalyst. The use of the particular catalyst quenching medium in the amounts disclosed herein can provide several advantageous features including reducing or eliminating the deposition of heavy fractions, waxes, and polymer byproducts of an oligomerization process in downstream equipment, and recycling the catalyst quenching medium. Furthermore, the catalyst quenching medium can be completely miscible with the product stream. Accordingly, there is no need for any aqueous/organic phase separation. Therefore, a substantial improvement in the catalyst deactivation of an olefin oligomerization catalyst is provided.

The processes disclosed herein include at least the following embodiments:

Embodiment 1

A process for deactivation of an olefin oligomerization catalyst, the process comprising: contacting a catalyst composition with a catalyst quenching medium comprising an alcohol having at least 6 carbon atoms, an organic amine, an amino alcohol, or a combination comprising at least one of the foregoing, to form a deactivated catalyst composition, wherein the catalyst quenching medium is present in a molar ratio of catalyst quenching medium to catalyst of at least 3:1, preferably at least 5:1, more preferably at least 100:1; and recovering excess catalyst quenching medium.

Embodiment 2

The process of Embodiment 1, further comprising recycling the recovered catalyst quenching medium.

Embodiment 3

The process of Embodiment 1 or Embodiment 2, wherein the catalyst composition comprises a chromium source, a heteroatomic multidentate ligand, an activator, and optionally, a modifier.

Embodiment 4

A process for the oligomerization of an olefin, the process comprising: feeding the olefin, a solvent, and a catalyst composition comprising a chromium source, a heteroatomic multidentate ligand, and an activator into a reactor; oligomerizing the olefin in the reactor to form a reaction product stream comprising linear alpha olefins, the solvent, and the catalyst composition; contacting the reaction product stream with a catalyst quenching medium comprising an alcohol having at least 6 carbon atoms, an organic amine, an amino alcohol, or a combination comprising at least one of the foregoing, to form a first intermediate stream comprising a deactivated catalyst composition, linear alpha olefins, the solvent, and excess catalyst quenching medium; separating the linear alpha olefins from the first intermediate stream to provide a second intermediate stream comprising the deactivated catalyst composition and excess catalyst quenching medium; and recovering the catalyst quenching medium from the second intermediate stream; wherein the catalyst quenching medium is contacted with the reaction product stream in a moles of catalyst quenching medium to moles of chromium source and activator ratio of at least 3:1, preferably at least 5:1, more preferably at least 100:1.

Embodiment 5

The process of Embodiment 4, wherein the olefin is ethylene.

Embodiment 6

The process of Embodiment 4 or Embodiment 5, wherein the solvent comprises at least one of toluene, xylene, mesitylene, ethyl benzene, n-pentane, n-hexane, and cyclohexane.

Embodiment 7

The process of any of Embodiments 3-6, wherein the chromium source is at least one of $CrCl_3(tetrahydrofuran)_3$, Cr(III)acetylacetonate, Cr(III)octanoate, chromium hexacarbonyl, Cr(III)-2-ethylhexanoate, benzene(tricarbonyl)-chromium, or Cr(III)chloride.

Embodiment 8

The process of any of Embodiments 3-7, wherein the heteroatomic multidentate ligand is $(phenyl)_2PN(iso-propyl)P(phenyl)N(iso-propyl)H$.

Embodiment 9

The process of any of embodiments 3 to 8, wherein the activator is a $tri(C_{1-6}$ alkyl) aluminum.

Embodiment 10

The process of any of Embodiments 3-9, wherein the modifier comprises tetraphenylphosphonium chloride, tetraethylammonium chloride-monohydrate, tetraethylammonium chloride, isopropylamine hydrochloride, triethylamine hydrochloride, tetrapropylammonium chloride, trimethyldodecylammonium chloride, tetra-n-butylammonium chloride, tetraethylammonium bromide, p-toluidine hydrochloride, dimethyldistearylammonium chloride and (tri-n-butyl)-n-tetradecylphosphonium chloride.

Embodiment 11

The process of any of Embodiments 1-9, wherein the catalyst composition is halogen-free.

Embodiment 12

The process of any of Embodiments 4-11, wherein the linear alpha olefins comprise $C_{4-12}$ linear alpha olefins.

Embodiment 13

The process of any of Embodiments 4-12, wherein the linear alpha olefins comprise at least one of 1-butene, 1-hexene, or 1-octene.

Embodiment 14

The process of any of Embodiments 4-13, wherein the catalyst quenching medium is miscible with the reaction product stream.

Embodiment 15

The process of any of Embodiments 1-14, wherein the catalyst quenching medium comprises a $C_{6-20}$ alkyl alcohol.

Embodiment 16

The process of any of Embodiments 1-15, wherein the catalyst quenching medium comprises at least one of 1-hexanol, 3-hexanol, 2-ethyl-1-hexanol, 3-octanol, 1-heptanol, 2-heptanol, 3-heptanol, 4-heptanol, 2-methyl-3-heptanol, 1-octanol, 2-octanol, 4-octanol, 7-methyl-2-decanol, 1-decanol, 2-decanol, 3-decanol, 4-decanol, 5-decanol, or 2-ethyl-1-decanol, preferably wherein the catalyst quenching medium comprises 1-decanol.

Embodiment 17

The process of any of Embodiments 1-16, wherein at least 60%, preferably at least 75%, more preferably at least 90% of the catalyst quenching medium is recovered.

Embodiment 18

The process of any of Embodiments 1-17, wherein the process further comprises recycling recovered catalyst quenching medium.

Embodiment 19

The process of any of Embodiments 4-18, wherein distillation is used for separating the linear alpha olefins and recovering the catalyst quenching medium.

Embodiment 20

The process of any of Embodiments 4-19, wherein separating the linear alpha olefins and recovering the catalyst quenching medium occur in different rectification columns.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

As used herein, the term "hydrocarbyl" includes groups containing carbon, hydrogen, and optionally one or more heteroatoms (e.g., 1, 2, 3, or 4 atoms such as halogen, O, N, S, P, or Si). "Alkyl" means a branched or straight chain, saturated, monovalent hydrocarbon group, e.g., methyl, ethyl, i-propyl, and n-butyl. "Aryl" means a monovalent, monocyclic, or polycyclic aromatic group (e.g., phenyl or naphthyl). "Substituted" means that the compound or group is substituted with at least one (e.g., 1, 2, 3, or 4) substituents instead of hydrogen, where each substituent is independently nitro ($-NO_2$), cyano ($-CN$), hydroxy ($-OH$), halogen, thiol ($-SH$), thiocyano ($-SCN$), $C_{1-6}$ alkyl, $C_{2-6}$ alkenyl, $C_{2-6}$ alkynyl, $C_{1-6}$ haloalkyl, $C_{1-9}$ alkoxy, $C_{1-6}$ haloalkoxy, $C_{3-12}$ cycloalkyl, $C_{5-18}$ cycloalkenyl, $C_{6-12}$ aryl, $C_{7-13}$ arylalkylene (e.g, benzyl), $C_{7-12}$ alkylarylene (e.g. toluyl), $C_{4-12}$ heterocycloalkyl, $C_{3-12}$ heteroaryl, $C_{1-6}$ alkyl sulfonyl ($-S(=O)_2$-alkyl), $C_{6-12}$ arylsulfonyl ($-S(=O)_2$-aryl), or tosyl ($CH_3C_6H_4SO_2-$), provided that the substituted atom's normal valence is not exceeded, and that the substitution does not significantly adversely affect the manufacture, stability, or desired property of the compound. When a compound is substituted, the indicated number of carbon atoms is the total number of carbon atoms in the group, including those of the substituent(s).

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A process for deactivation of an olefin oligomerization catalyst, the process comprising:
    contacting the olefin oligomerization catalyst with a catalyst quenching medium comprising an alcohol having at least 6 carbon atoms, an organic amine, an amino alcohol, or a combination comprising at least one of the foregoing, to form a deactivated catalyst composition, wherein the catalyst quenching medium is present in a molar ratio of catalyst quenching medium to the olefin oligomerization catalyst of at least 100:1; and
    recovering excess catalyst quenching medium.

2. The process of claim 1, further comprising recycling the recovered catalyst quenching medium.

3. The process of claim 1, wherein the catalyst composition comprises a chromium source, a heteroatomic multidentate ligand, an activator, and optionally, a modifier.

4. The process of claim 1, wherein the catalyst composition is halogen-free.

5. The process of claim 1, wherein the catalyst quenching medium comprises a $C_{6-20}$ alkyl alcohol.

6. The process of claim 1, wherein the catalyst quenching medium comprises at least one of 1-hexanol, 3-hexanol, 2-ethyl-1-hexanol, 3-octanol, 1-heptanol, 2-heptanol, 3-heptanol, 4-heptanol, 2-methyl-3-heptanol, 1-octanol, 2-octanol, 4-octanol, 7-methyl-2-decanol, 1-decanol, 2-decanol, 3-decanol, 4-decanol, 5-decanol, or 2-ethyl-1-decanol.

7. The process of claim 1, wherein at least 60% of the catalyst quenching medium is recovered.

8. A process for the oligomerization of an olefin, the process comprising:
    feeding the olefin, a solvent, and a catalyst composition comprising a chromium source, a heteroatomic multidentate ligand, and an activator into a reactor;
    oligomerizing the olefin in the reactor to form a reaction product stream comprising linear alpha olefins, the solvent, and the catalyst composition;
    contacting the reaction product stream with a catalyst quenching medium comprising an alcohol having at least 6 carbon atoms, an organic amine, an amino alcohol, or a combination comprising at least one of the foregoing, to form a first intermediate stream comprising a deactivated catalyst composition, linear alpha olefins, the solvent, and excess catalyst quenching medium;
    separating the linear alpha olefins from the first intermediate stream to provide a second intermediate stream comprising the deactivated catalyst composition and excess catalyst quenching medium; and
    recovering the catalyst quenching medium from the second intermediate stream;
    wherein the catalyst quenching medium is contacted with the reaction product stream in a molar ratio of catalyst quenching medium to the catalyst composition of at least 100:1.

9. The process of claim 8, wherein the olefin is ethylene.

10. The process of claim 8, wherein the solvent comprises at least one of toluene, xylene, mesitylene, ethyl benzene, n-pentane, n-hexane, and cyclohexane.

11. The process of claim 3, wherein the chromium source is at least one of $CrCl_3$(tetrahydrofuran)$_3$, Cr(III)acetylacetonate, Cr(III)octanoate, chromium hexacarbonyl, Cr(III)-2-ethylhexanoate, benzene(tricarbonyl)-chromium, or Cr(III)chloride.

12. The process of claim 3, wherein the heteroatomic multidentate ligand is (phenyl)$_2$PN(iso-propyl)P(phenyl)N(iso-propyl)H.

13. The process of claim 3, wherein the activator is a tri($C_{1-6}$ alkyl) aluminum.

14. The process of claim 3, wherein the modifier comprises tetraphenylphosphonium chloride, tetraethylammonium chloride-monohydrate, tetraethylammonium chloride, isopropylamine hydrochloride, triethylamine hydrochloride, tetrapropylammonium chloride, trimethyldodecylammonium chloride, tetra-n-butylammonium chloride, tetraethylammonium bromide, p-toluidine hydrochloride, dimethyldistearylammonium chloride and (tri-n-butyl)-n-tetradecylphosphonium chloride.

15. The process of claim 8, wherein the linear alpha olefins comprise $C_{4-12}$ linear alpha olefins.

16. The process of claim 8, wherein the linear alpha olefins comprise at least one of 1-butene, 1-hexene, or 1-octene.

17. The process of claim 8, wherein the catalyst quenching medium is miscible with the reaction product stream.

18. The process of claim 8, wherein the process further comprises recycling recovered catalyst quenching medium.

19. The process of claim 8, wherein distillation is used for separating the linear alpha olefins and recovering the catalyst quenching medium.

20. The process of claim 8, wherein separating the linear alpha olefins and recovering the catalyst quenching medium occur in different rectification columns.

\* \* \* \* \*